US008945073B2

(12) United States Patent
Croizat et al.

(10) Patent No.: US 8,945,073 B2
(45) Date of Patent: Feb. 3, 2015

(54) VACUUM GENERATION DEVICE FOR MEDICAL APPLICATIONS

(75) Inventors: Pierre Croizat, Herbrechtingen (DE); Axel Eckstein, Heidenheim (DE); Marc Roettger, Bad Boll (DE)

(73) Assignee: Paul Hartmann AG, Heidenheim (DE)

( * ) Notice: Subject to any disclaimer, the term of this patent is extended or adjusted under 35 U.S.C. 154(b) by 503 days.

(21) Appl. No.: 13/369,343

(22) Filed: Feb. 9, 2012

(65) Prior Publication Data

US 2012/0209228 A1    Aug. 16, 2012

Related U.S. Application Data

(60) Provisional application No. 61/457,844, filed on Jun. 17, 2011.

(30) Foreign Application Priority Data

Feb. 10, 2011    (DE) .......................... 10 2011 011 831

(51) Int. Cl.
*A61M 1/00*    (2006.01)

(52) U.S. Cl.
CPC ........... *A61M 1/0023* (2013.01); *A61M 1/0003* (2013.01); *A61M 1/0088* (2013.01); *A61M 2209/082* (2013.01); *A61M 2209/088* (2013.01)
USPC ............ 604/315; 604/319; 604/322; 604/326

(58) Field of Classification Search
CPC ............ A61M 1/0001; A61M 1/0003; A61M 1/0023; A61M 1/0066; A61M 2209/08; A61M 2209/082; A61M 2209/084; A61M 2209/086
USPC .......................... 604/313, 315, 319, 322, 326
See application file for complete search history.

(56) References Cited

U.S. PATENT DOCUMENTS

| | | | | |
|---|---|---|---|---|
| 4,086,925 | A * | 5/1978 | Dodge .......................... | 604/326 |
| 4,312,352 | A * | 1/1982 | Meisch et al. ................. | 604/322 |
| 5,134,994 | A * | 8/1992 | Say .......................... | 128/200.24 |
| 5,588,958 | A * | 12/1996 | Cunningham et al. ....... | 604/6.15 |
| 6,368,311 | B1 * | 4/2002 | Valerio et al. ................. | 604/322 |
| 7,004,915 | B2 * | 2/2006 | Boynton et al. .................. | 601/6 |
| 7,232,105 | B2 * | 6/2007 | Want et al. ..................... | 248/691 |
| 7,670,323 | B2 * | 3/2010 | Hunt et al. ..................... | 604/313 |
| 7,699,831 | B2 * | 4/2010 | Bengtson et al. ............. | 604/541 |

(Continued)

FOREIGN PATENT DOCUMENTS

| DE | 10 2009 038 131 | 2/2011 |
|---|---|---|
| EP | 0 100 672 | 2/1984 |

(Continued)

*Primary Examiner* — Lynne Anderson
(74) *Attorney, Agent, or Firm* — Paul Vincent

(57) ABSTRACT

A device (2) for generating a vacuum for vacuum therapy of wounds has a facility for generating a vacuum and a vessel (10) for receiving wound exudates suctioned out of a wound. The vessel (10) can be detachably fastened to the device. A connection (12) is provided for a suction tube, the suction tube leading to the body to establish vacuum communication among the facility generating the vacuum, the vessel (10) and the suction tube. A holding facility (102) provides for detachable fastening of the device (2) onto a strut or bar and comprises an essentially rigid holding part (104), which can be attached to a housing (4) of the device and which has a receptacle (106) for detachable disposition of a flexible holding strap (108). The holding strap (108) can be wrapped around the strut or bar through application of a tensile force.

20 Claims, 14 Drawing Sheets

(56) References Cited

U.S. PATENT DOCUMENTS

| | | | |
|---|---|---|---|
| 8,048,046 B2 * | 11/2011 | Hudspeth et al. | 604/313 |
| 8,444,612 B2 * | 5/2013 | Patel et al. | 604/313 |
| 2011/0040288 A1 | 2/2011 | Eckstein | |
| 2011/0168857 A1 | 7/2011 | Svedman | |

FOREIGN PATENT DOCUMENTS

| | | |
|---|---|---|
| EP | 0 263 664 | 4/1988 |
| EP | 1 905 465 | 4/2008 |
| WO | WO 2008/036344 | 3/2008 |
| WO | WO 2009/103031 | 8/2009 |

* cited by examiner

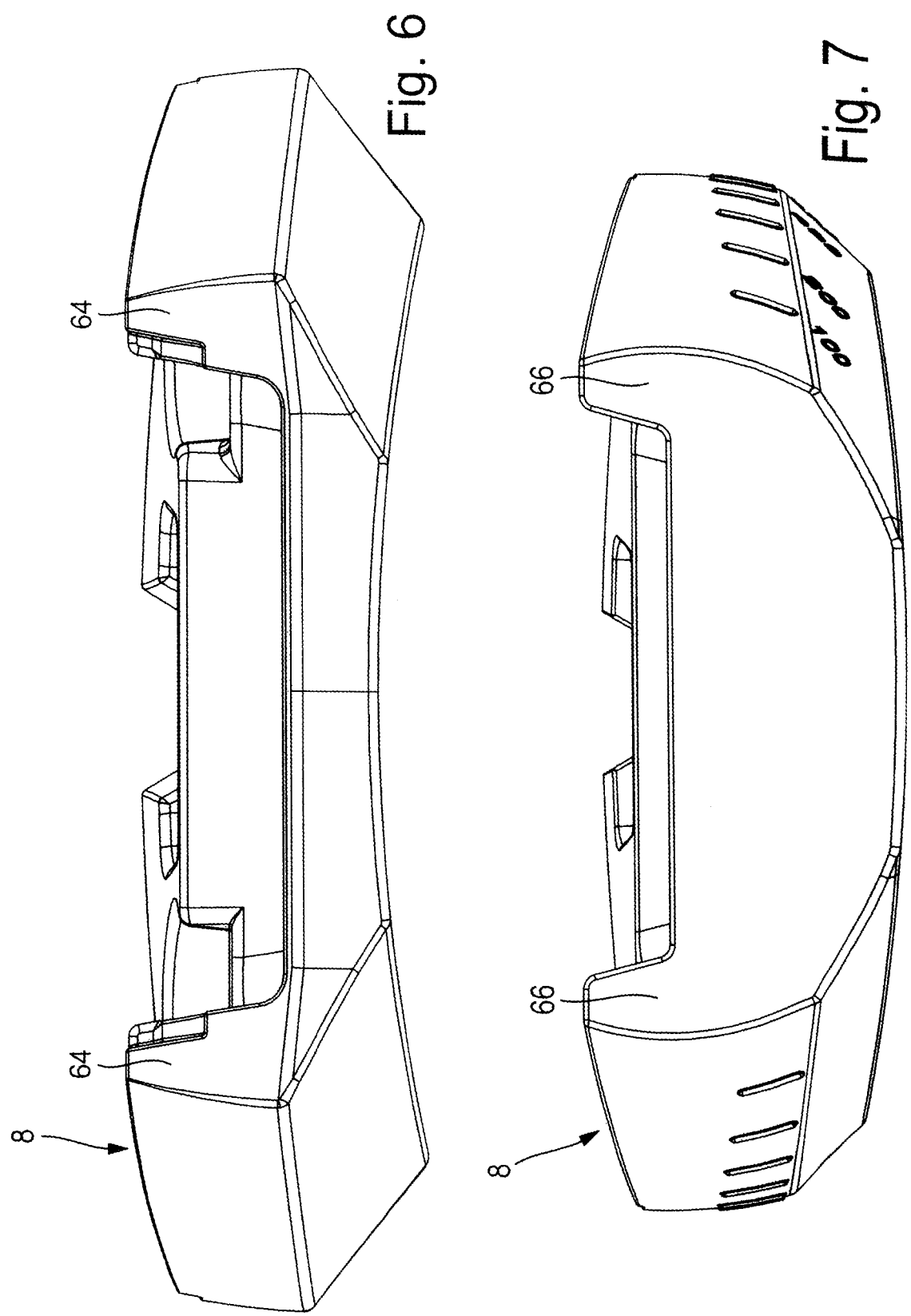

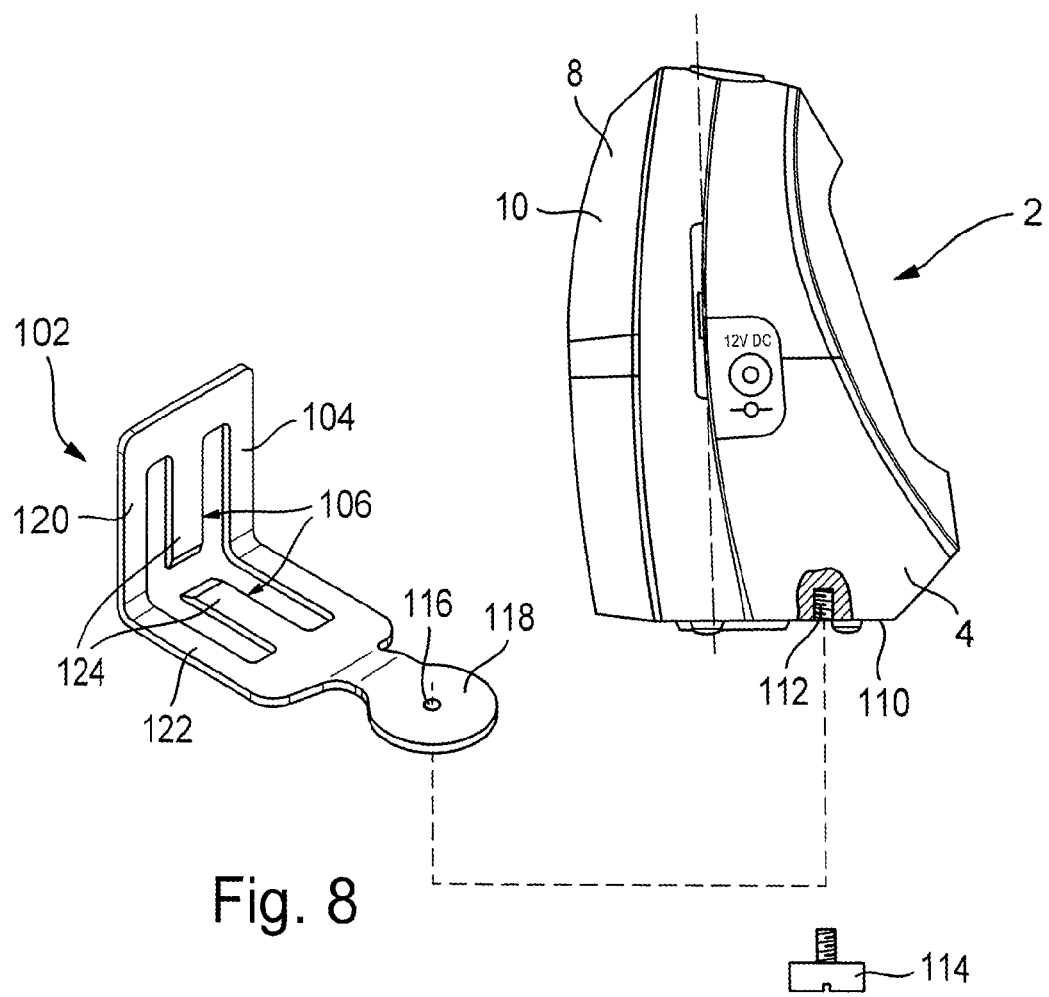
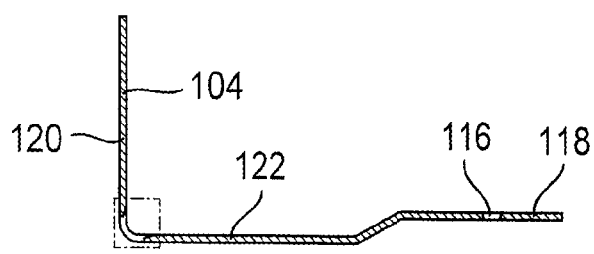
Fig. 9a
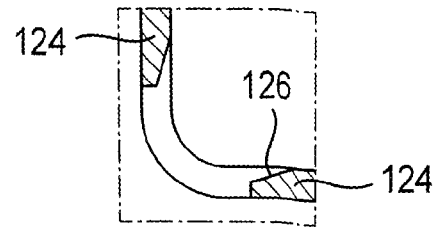
Fig. 9b

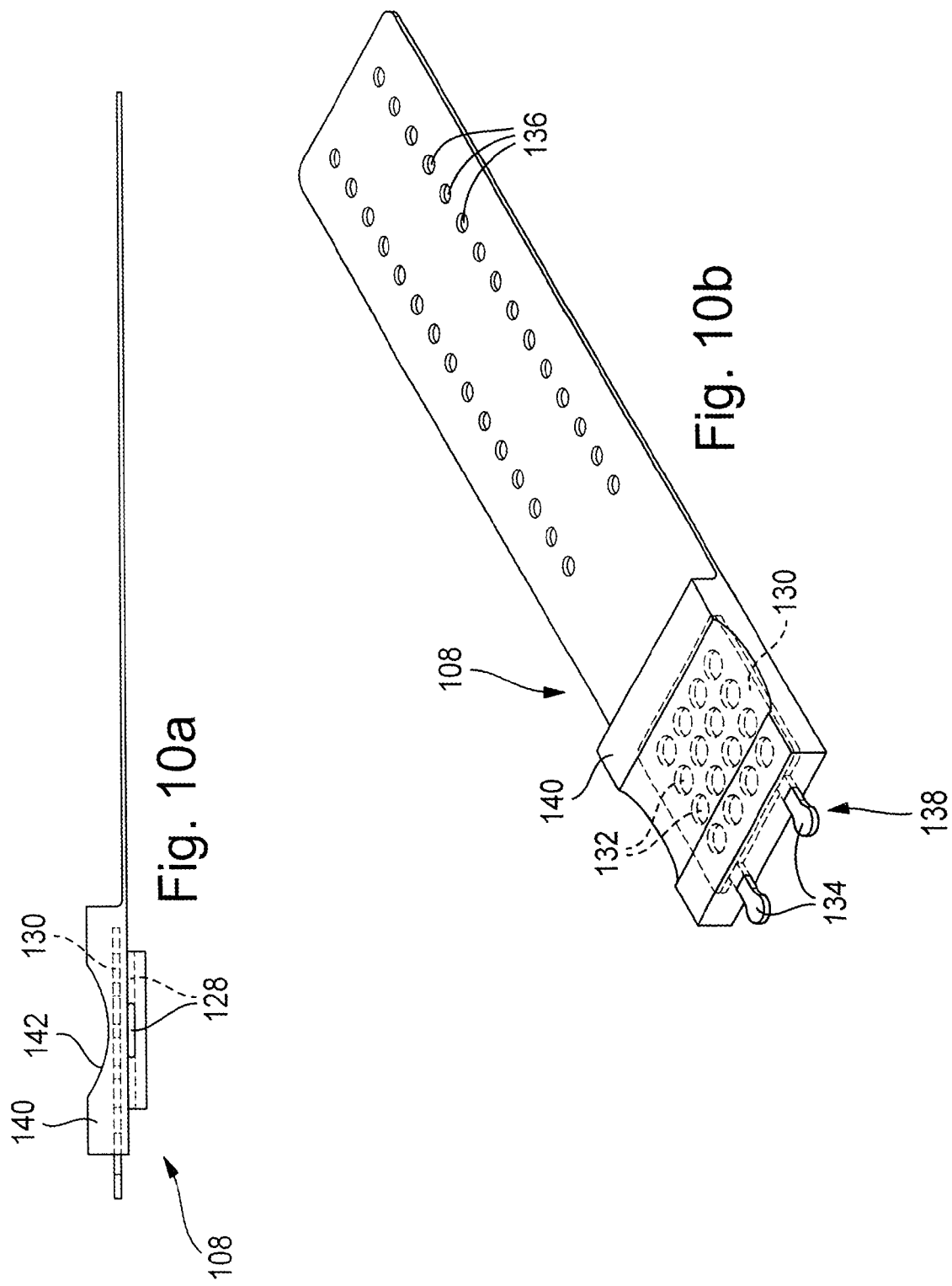

VACUUM GENERATION DEVICE FOR MEDICAL APPLICATIONS

This application claims benefit of 61/457,844 filed Jun. 17, 2011 as well as Paris Convention priority of DE 10 2011 011 831 filed Feb. 10, 2011 the entire disclosures of which are hereby incorporated by reference.

BACKGROUND OF THE INVENTION

The invention relates to a device for generating a vacuum for medical applications, in particular, for the vacuum therapy of wounds on a human or animal body, with a facility for generating a vacuum and a vessel, which is typically disposable after use, to receive body fluids, in particular wound exudates suctioned out of a wound, wherein the vessel can be detachably fastened to the device and wherein a connection for a suction tube leading to the body is provided, so that vacuum communication between the facility generating the vacuum, the vessel, and the suction tube leading to the body can be established, and with a holding facility for detachable fastening of the device on a horizontal or vertical or oblique strut or bar.

Devices for vacuum wound therapy have already been described several times, in particular by US 2004/0073151 A1, WO 2009/047524 A2, WO 2007/030599 A2 or EP 1 905 465 A1 and by the non-prepublished patent applications DE 10 2009 038 130.9 and DE 10 2009 038 131.7 of the assignee.

In such devices for the vacuum therapy of wounds, a vacuum-generating device communicates via a suction tube with the wound or the surroundings of the wound, wherein cover material that is impervious to air is provided to ensure air-tight sealing of the wound and the surroundings of the wound so that a vacuum can be established in the wound space and liquids can be suctioned out of the wound space into the vessel.

The term vacuum in connection with this invention refers to a lower air pressure than the ambient air pressure (atmospheric pressure), in particular inside the wound dressing. The cover material of a wound dressing for air-tight closure of a wound space must therefore be constituted such that it can withstand the established pressure difference so that the vacuum in the wound space can be produced in the first instance and then maintained. In vacuum therapy for wound treatment, the vacuum is quantitatively expressed as the pressure difference between the ambient air pressure and the air pressure applied beneath the cover material. In vacuum therapy, this pressure difference is typically no more than 250 mm Hg (mm of mercury) (1 mm Hg=1 Torr=133.322 Pa). This vacuum range not exceeding 250 mm Hg has proven advantageous for wound healing. A preferred vacuum range is between 10 and 150 mm Hg.

The vacuum applied to the wound using the device can, in typical vacuum therapy, either be kept essentially constant over time or it can vary over time, in particular, cyclically, which can be implemented using an appropriately constituted and programmed control device on the facility producing the vacuum, in particular, in dependence on further parameters.

To apply the vacuum and preferably also to suction away body fluids, a preferably flexible suction tube, for example, in the form of a drainage tube, is provided that communicates at one end through a port in the region of the wound cover material with the wound environment or the wound space and at the other end with the vessel stated above for receiving body fluids or with the facility producing the vacuum.

In addition to the vacuum therapy of wounds, other applications of the device described here are conceivable for providing a vacuum for medical applications, in particular, the removal by suction of any body fluids in medical incontinent care, the care of stoma patients, or for the removal by suction of wound exudates, possibly, using rinsing liquids, and also without the application of a vacuum over considerable periods of time.

WO 2008/036344 A1 has already proposed firmly clamping the device on a bar or strut of a patient bed by means of clamping or wing screws, wherein a clamping arm that can be swiveled through 90° is described to permit fastening to a vertical or horizontal strut of the patient bed. Simply hanging the device by means of a hook has also been previously disclosed.

The object of this invention is to provide a reliable and simple to implement a way of fastening the device.

SUMMARY OF THE INVENTION

This object is inventively achieved with a device of the type stated above by means of a holding facility that comprises an essentially rigid holding part, which can be attached to a housing of the device by positive joint and/or by clamping and can be detached therefrom, and which has a receptacle for detachable disposition of a flexible, preferably elastically compliant ribbon-shaped holding means, which can be placed around a horizontal or vertical or oblique strut or bar and can be turned back on itself or onto the holding part and can be closed in such a way that, by exerting a tensile force on the holding means and by closing the holding means, essentially clearance-free and clamped fastening of the device to the strut or bar can be achieved.

According to the invention, it is therefore proposed that the holding facility not be integrated into the device or into the device housing as a non-detachable integral part, which would increase the total weight of the device. This would be a disadvantage in devices for generating a vacuum that are not intended for use only as a stationary item of equipment but also intended for use as devices that can be worn on the body of the patient and are therefore portable. Because the holding facility, i.e. the essentially rigid holding part, can be detachably fastened to a housing of the device, it can be removed from the housing along with the flexible ribbon-shaped holding means if the device is used in mobile operation and is carried by a patient.

To fasten the holding facility to the housing of the device via its essentially rigid holding part, any positive-joint and/or clamping methods of fastening may be used, wherein a screw fastening is preferred. In this case, the rigid holding part can have a through-hole for a screw so that the holding part can be fastened preferably by means of a clamping screw that can be tightened and released manually and without the use of tools and engages in a corresponding threaded hole on the device housing. The rigid holding part is advantageously mounted against the underside of the device housing.

Although the essentially rigid holding part can be made of various conceivable materials and can have various geometries or shapes that are adapted to the device, it proves advantageous if it is formed from a single flat and thin material section. In this case, it may, in particular, be a bent and punched metal part, which can be manufactured very simply and at low cost and also provides a load carrying capacity that meets the requirements for the device for generating a vacuum.

As has already been stated, the holding part supports the device on one side and, on the other side, holds or provides mounting for the flexible, preferably elastically compliant ribbon-shaped holding means by which the device can simply be attached to a horizontal or vertical strut of a patient bed or an infusion stand.

For this purpose, it proves advantageous if, in a further embodiment of the invention, the receptacle constituted on the holding part for detachable disposition of the flexible ribbon-shaped holding means has a sliding-seat configuration permitting the ribbon-shaped holding means to be slid onto the rigid holding part in a linear direction.

For this purpose, it further proves advantageous if the receptacle constituted on the holding part has at least one finger-shaped or tongue-shaped web, in particular a flat web, which engages in a duct-forming cutout of the holding means when the flexible ribbon-shaped holding means is pushed on. If the finger-shaped or tongue-shaped web tapers, that is, in particular ends in a bevel, this will make it easier to slide on the flexible ribbon-shaped holding means.

According to a further especially advantageous inventive idea, it is proposed that the receptacle constituted on the holding part be constituted such that the flexible ribbon-shaped holding means can be fastened in two orientations of a longitudinal axis of the ribbon that extend at 90° to each other. In this way, fastening around a horizontal or vertical strut can be adjusted without altering the positioning of the rigid holding part.

According to a further, especially significant inventive idea, it proves advantageous if the essentially rigid holding part has at least two receptacles, each for the detachable disposition of one flexible ribbon-shaped holding means, wherein the receptacles are oriented in such a way that the ribbon-like holding means are aligned at an angle of preferably 90° with respect to each other and with respect to the device. In this way, it is inventively achieved that not just one but two ribbon-shaped holding means can be fastened in different orientations on the one rigid holding part. This provides a total of at least two ribbon-shaped holding means for fastening the device housing on a bar or strut.

According to a further, especially significant inventive idea, it is proposed that the essentially rigid holding part have an angular shape. In this case, as a further embodiment of this idea, it proves advantageous if a receptacle for detachable disposition of one flexible ribbon-shaped holding means is constituted on each leg of the angle-shaped holding part. If this receptacle advantageously has a sliding-seat configuration, as mentioned above, it proves advantageous if the sliding-seat receptacle or its finger-shaped or tongue-shaped webs are mutually aligned toward the apex of the angle. Because of the angular shape, which is preferably 90°, additional relative orientation in space of the relevant ribbon level of the flexible ribbon-shaped holding means can be defined. This can prove advantageous in that it provides the greatest possible adaptability of the holding facility in various mounting situations in practical use.

The flexible ribbon-shaped holding means is, as has already been mentioned, preferably constituted to be elastically compliant, in particular with rubber elasticity. It may then advantageously be made of a rubber-like, in particular, silicone-like material, wherein also other materials, in particular, polymer-based materials or composite materials can be used.

To provide the attachability of the flexible ribbon-shaped holding means in preferably different orientations on the receptacle of the rigid holding part in a manner that is suitable for the purpose and user-friendly, it is proposed that the flexible ribbon-shaped holding means have a duct-forming cutout or two preferably mutually perpendicularly oriented duct-forming cutouts. In this manner, the holding means can be positioned in a single mounting operation that is accessible to everyone. In this case, the device can also easily be fastened or detached by a patient having little training, for example, when carried on the body of the patient in mobile use.

If also proves advantageous if the flexible ribbon-shaped holding means has a mechanical-action closing means so that it can be closed by turning it back on itself or onto the holding part.

For example, it would be at least basically conceivable to use mechanical closing means based on a hook-and-loop closing material. With regard to secure fixture, it proves advantageous if the mechanical-action closing means is constituted by at least one projection on one side and, on the other side, by through-holes, into which the projection can engage to achieve a secure preloaded positive-joint closing action. The preferably multiple through-holes are then preferably provided and constituted according to a pattern in the ribbon material of the ribbon-like holding means. The above-mentioned at least one projection can be constituted on the rigid holding part and/or on the flexible ribbon-shaped holding means. According to one embodiment, the at least one projection extends in a plane of the flexible ribbon-shaped holding means or in a plane of the rigid holding part.

According to a further especially advantageous inventive idea, it is proposed that the flexible ribbon-shaped holding means have a reinforcing part constituted as a rigid, preferably metal, in particular, injection molded part. This reinforcing part is preferably wide and flat and has holes for better overmolding or laminating. In such a case, it proves advantageous if the reinforcing part forms the at least one projection, i.e. that projection is constituted integrally with this reinforcing part. In this case, the projection extends over a surface or edge of the material constituting the ribbon-like holding means.

It further proves especially advantageous if the flexible ribbon-shaped holding means has a thicker region that is constituted with 3-dimensional contouring, in the transverse direction with respect to the ribbon plane, to form a compliant contact zone for contacting a bar or strut. In this case, the contact zone is conveniently constituted on the side of the flexible ribbon-shaped holding means that is located opposite the holding part.

According to a further inventive idea, the rigid holding part is constituted such that the detachable vessel for receiving liquids is provided between the receptacle of the rigid holding part for the ribbon-like holding means and the housing of the device. The angular shape of the rigid holding part mentioned above is especially suitable for this embodiment and enables it to extend in the depth direction above or below the mounting space for detachable disposition of the vessel.

It also proves advantageous if the device for generating a vacuum for medical applications is constituted as described in the non-prepublished patent applications DE 10 2009 038 130.9 and DE 10 2009 038 131.7 of the applicant. Reference is therefore made to the entire disclosed content of these applications with respect to the constitution of the device with the exception of the holding facility not described there. The entire disclosure of those applications is hereby incorporated by reference. The following is described therein.

In particular, it is also advantageous if both housing parts are essentially constituted as disk-shaped and lie one against the other in an essentially vertically oriented separation plane. For the purpose of this invention, the disk shape of the two housing parts means that the housing parts, when they are set down as intended during stationary operation with their standing side on a horizontal support surface, each have a width and height that is larger than their depth when viewed horizontally. Therefore, when they are separably fixed together, the housing parts rest one against the other with the side that is in the disk plane. The separation plane stated above does not necessarily mean that the housing parts lie against one other on a precisely flat surface. Rather, protrusions advantageously acting as centering means or similar shaped elements can be provided on the housing parts in preferably complementary shapes. According to the invention, the two housing parts are therefore neither inserted into one another nor stacked one upon the other but lie side by side and one against the other on the aforementioned essentially vertically oriented separation plane when the device is set down as intended with its standing side on a horizontal surface or is carried on the body of a person standing upright as a mobile device. In the latter case, the first housing part is positioned facing away from the body and the second housing part facing toward the body when the device is being used carried on the body of the user (mobile operation).

Because, in mobile operation of the device, the vessel forming the second housing part or disposed in or on the second housing part together with the second housing part is oriented facing toward the body and the first housing part accommodating the vacuum-generating facility is facing away from the body, it is possible to cover the second housing part by means of the first housing part. In this way, the second housing part or the vessel could also be constituted to be transparent without permitting third parties to see directly inside. Moreover, the configuration of the second housing part in the region of the body affords greater design options for adaptation to the body than would be the case for the first housing part accommodating the vacuum-generating facility. Furthermore, due to the configuration of the first housing part facing away from the body, access can be provided to the operating elements for the vacuum-generating facility and its control on the visible side of the device. In this way, access to the device itself by the user is also possible by disposing the operating components and possibly also display components facing away from the body and preferably visible from above.

For user-friendly joining of the first and the second housing parts, it proves advantageous if the first and the second housing parts have centering means on their sides facing each other and if the housing parts can be joined together essentially transversely with respect to the separation plane. These centering means can be constituted in any way, for example, by pin-shaped or cone-shaped elements or by protruding and recessed housing regions that can, in particular, also be constituted in the shape of a block or box and preferably interact in a complementary way and with appropriate lead-in bevels to ensure centering. These centering means or the contacting sides of the housing parts are preferably constituted in such a way that they can only be joined in the correct manner.

To join the housing parts, it proves advantageous if the one housing part can be placed on a contact surface of the other housing part from above with a slightly upward inclination with respect to the vertical and can then be pivoted essentially transversely with respect to the separation plane into contact with the other housing part.

It proves essentially advantageous if, when joining the first and the second housing parts, vacuum communication is simultaneously established between the vessel and the vacuum-generating facility so that the joining operation is user-friendly overall and the user does not come into contact with body fluids. Analogously, this idea is even more important when separating the housing parts after use.

To keep the two housing parts reliably in contact, it proves advantageous if they can be separably fixed to each other by snap-in, latching, or other positive-action locking or back-gripping means.

According to one embodiment of the invention, it proves advantageous that the locking or back-gripping means projects from the separation plane of one of the housing parts and can be deflected transversely with respect to the joining direction of the housing parts during joining of the housing parts and can be put into a back-gripping position.

In a further embodiment of the invention, the locking or back-gripping means can be moved in a release direction by a manually operable operating element. The manually operable element can be disposed at any position on the device. However, it proves advantageous if it is provided on the top side of the device and, in particular, as a button that can be pressed in. In this way, it is possible to set down the device on a preferably horizontal surface and then to operate the operating element successfully without the device sliding away to the side.

To hold, lift, or handle the device as a whole and/or only one of the housing parts, it proves advantageous if one housing part is constituted for manual gripping so that the device or only the relevant housing part can be gripped in this manner and can be separated from the other housing part. It proves especially advantageous if the second housing part has a grip cavity or grip recess for this purpose. This grip cavity or grip recess is preferably provided in the region of a manually operable operating element for a locking or back-gripping means so that a user or a caregiver can, with only one hand, unlock the second vessel part and separate it from the first vessel part. This grip cavity or grip recess is preferably provided in an upper region of the second housing part inclined away from the body on the side of the second housing part facing the body. In this way, the user is easily able to grip the device with one hand during mobile operation and to release a belt-like fastening means, to be described below, with the other hand.

To ensure the device stands firmly during stationary operation or when the device is temporarily set down on a preferably flat surface, it proves advantageous if a center of gravity of the device (while the vessel is still unused) is in the lower half of the device, that is, below an imaginary horizontal central plane, half way up the device.

To achieve this, it proves advantageous if the ratio of the standing surface of the device to its height is 4.0-6.0 $cm^2$/cm, in particular, 4.5-5.5 $cm^2$/cm. The standing surface of the device can, for example, be approximately 81 $cm^2$ and its height approximately 16 cm.

It is conceivable and advantageous for many applications if the standing surface of the device is constituted by both housing parts when its two housing parts are joined together. However, in a further embodiment of the invention, it has proven sufficient if the standing surface of the device is only formed by the first housing part. For this purpose, it proves advantageous if the first housing part forms a region projecting into a form recess of the first housing part that forms part of the standing surface. In this way, it is ensured after the first housing part has been removed from the second housing part that the vacuum-generating facility and its control components continue to stand as firmly as they did before.

According to a further inventive idea, it is proposed that the device be constituted in such a way that the first housing part covers the second housing part, when viewed from the front onto a visible side of the first housing part facing away from the body, preferably completely or at least covering 90% of the visible surface in this viewing direction. This further enables the second housing part to be constituted inexpensively because it is only visible to the user or to third parties to a small extent in the region of its side surfaces when the device is worn on the body of the user. The vessel therefore no longer has to be "concealed" in carrying bags.

According to an especially important inventive idea, it is proposed that the device comprise a plurality of second housing parts each with a vessel as a sort of collective item that are selectively connectable with the first housing part to form the device, wherein the second housing parts and their vessels are of different sizes, in particular, in the depth direction, that is, toward the user. In this way, different holding capacities can be provided by different housing parts and their vessels. Housing parts can be provided for this that are suitable for mobile operation and others that are more suitable for stationary operation, that is, in particular, those with a larger volume so that the vessels require less frequent replacement when receiving liquids.

It further proves advantageous if the holding facility and its rigid holding part are constituted in such a way and can be fastened to the housing in such a way that the vessel, or also variously dimensioned vessels, can be removed from the housing or mounted thereon without any need to detach the holding facility for the device. If variously dimensioned vessels are used, the holding facility and its rigid holding part are constituted in such a way that the variously dimensioned vessels all equally "have room" and can be replaced.

It further proves advantageous if a filling level indicator is provided for the vessel. This filling level indicator can, for example, be implemented by a sufficiently transparent housing wall of the second housing part or it can be constituted in any other way, in particular, using electronic sensors and display means. A monitoring facility also proves advantageous that outputs an alarm depending on the filling level reached in the vessel. The vessel of the second housing part can contain a superabsorbent medium to bind the suctioned-in liquid and to prevent the liquid from sloshing.

It has already been pointed out that the inventive embodiment of the device advantageously allows operating elements and display elements for the vacuum-generating facility to be provided on a visible side of the first housing part facing away from the body. The operating elements are advantageously constituted in the form of a touchscreen.

According to a further inventive idea of great importance, it proves advantageous if the entire visible side of the first housing part facing away from the body is essentially constituted or overlapped by a large-surface cover to avoid dirt-trapping joints in the region of the operating elements.

It further proves advantageous if the housing parts in the joined condition of the device do not have any back-grippable components on the outer side, with the exception of the connection for the suction tube or a measuring or rinsing duct and any grip cavity or grip recess.

Further characteristics, details, and advantages can be derived from the drawings and the following description of an inventive device for generating a vacuum for medical applications with a holding facility for detachable fastening of the device to a strut or bar, or the like. The drawing shows:

BRIEF DESCRIPTION OF THE DRAWING

FIGS. 6, 7 a view of the second housing part of the devices according to FIGS. 1 and 4 from below to illustrate the different standing surfaces of these second housing parts;

FIG. 8 shows an inventive device with a rigid holding part of a holding facility;

FIGS. 9a, b two views of the rigid holding part according to FIG. 8;

FIGS. 10a-c views of a flexible ribbon-shaped holding means of the holding facility;

DESCRIPTION OF THE PREFERRED EMBODIMENT

Figure 1A:
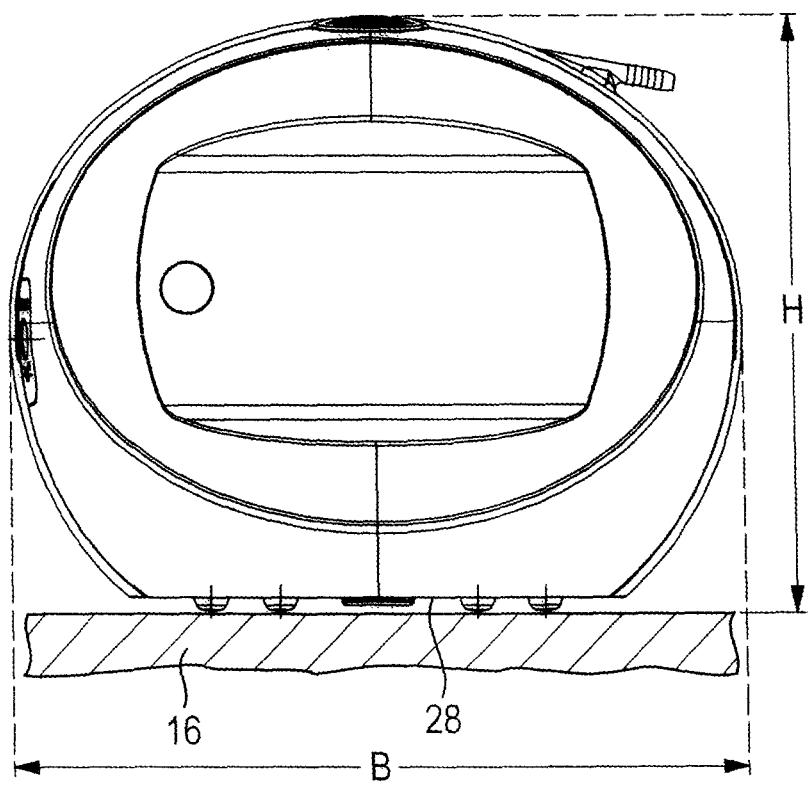
FIGS. 1a to e various views of a preferred embodiment of a device for carrying on the body to generate a vacuum for medical applications.
Figure 1B:
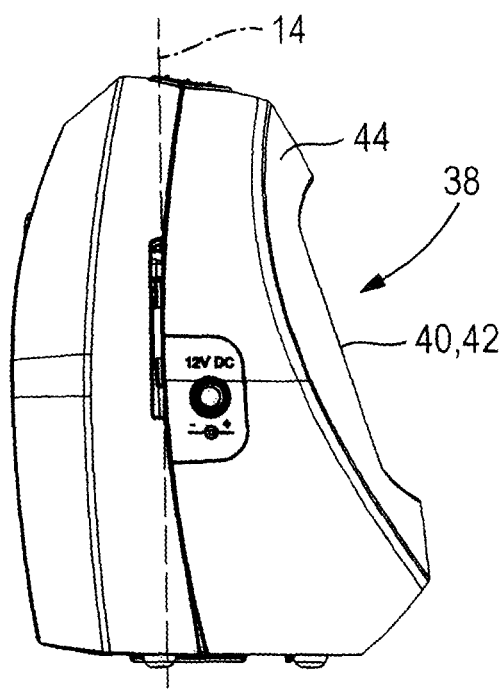

FIGS. 1a to e show a first embodiment of an inventive portable device 2 for generating a vacuum for medical applications. The device comprises a first housing part 4 in which a vacuum-generating device in the form of an air pump and electrical and electronic control components for the device are accommodated completely, including batteries or preferably rechargeable batteries. A recharging connection for the batteries is designated by reference symbol 6. Moreover, the device 2 comprises a second housing part 8 that preferably is also a vessel 10 for receiving body fluids, in particular, for receiving wound exudates suctioned away from a wound. The entire second housing part 8 is preferably constituted as a disposable single-use item. In its upper region, a connection gland 12 for a suction tube, not depicted, is provided that can, for example, lead to a wound dressing that closes the wound pressure-tight when the device 2 is used in the vacuum therapy of wounds and there it can, for example, communicate with the wound space through a port to apply and maintain a vacuum to the wound space and to suction away wound exudates into the vessel 10. For this purpose, the vessel 10 communicates with the vacuum-generating facility. Further, a connection 13 is shown for an optional measuring or rinsing duct that is guided to the wound, like the suction tube. This connection passes through the second housing part 8 and exits into the first housing part 4, from where, for example, air as the rinsing medium can be applied to the measuring or rinsing duct and/or pressure in this measuring or rinsing duct can be detected and evaluated.

Figure 1C:
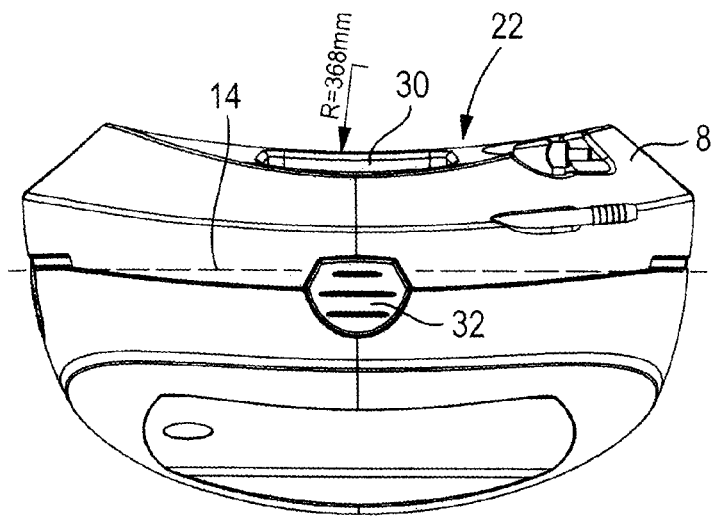
Figure 1D:
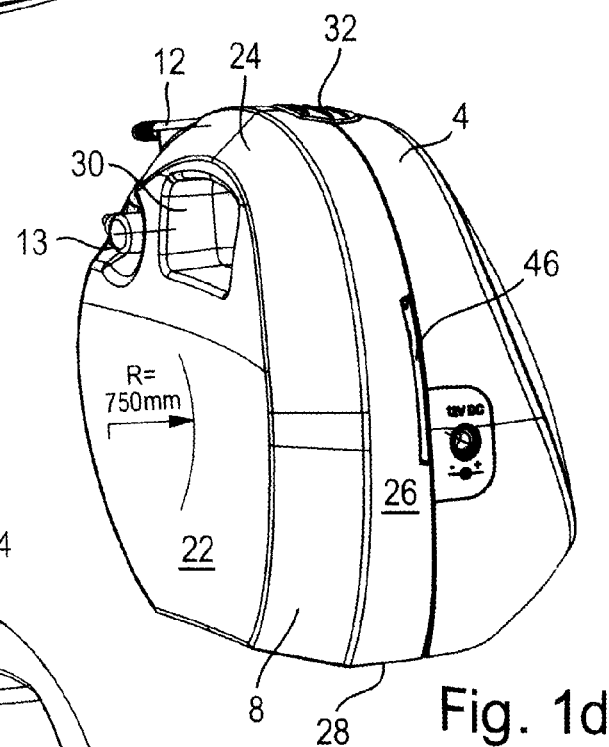
Figure 1E:
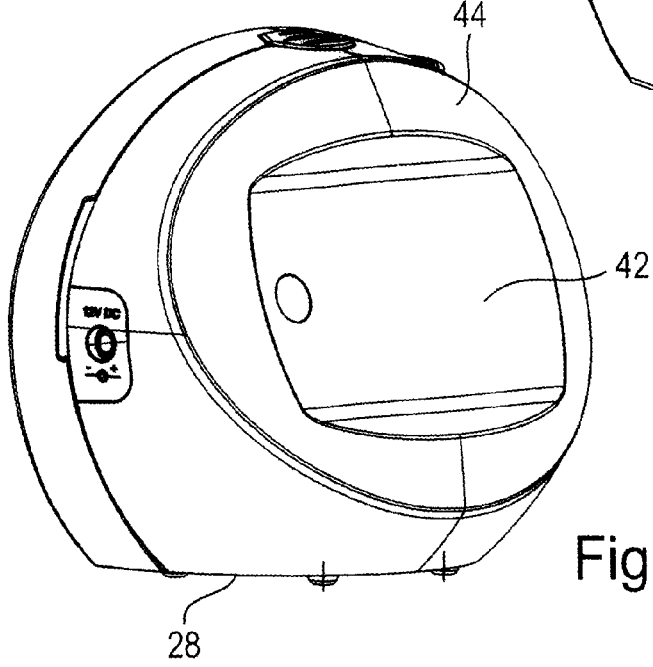

In the preferred case, the housing parts 4 and 8 lie one against the other on an essentially vertical separation plane 14 that is indicated in the various figures. When the device 2 is set down on an even horizontal surface 16, as shown in FIG. 1a, the separation plane 14 is oriented essentially vertically. This means that the two housing parts 4, 8 are not inserted one into the other nor stacked one upon the other, but that they remain side by side when the device 2 is joined as intended. The term separation plane 14 is therefore not to be understood as a geometrically level surface, as can be seen directly from FIGS. 2a to e, which show the first housing part 4 in various views. It is immediately apparent that the side 18 of the first housing part 4 facing the second housing part 8 is not flat but formed with a multiplicity of elements projecting toward the second housing part 8. The side 20 of the second housing part 8 facing the first housing part 4 is constituted essentially complementarily to the shape of the side 18 of the first housing part 4 so that the two housing parts 4, 8 can only be joined and fastened together in the correct manner. The two housing parts 4, 8 are constituted disk-shaped overall, that is, their width B in the horizontal direction and their height H in the vertical direction are larger than their depth T in the horizontal direction and perpendicular to the extent of the width. In this way, it is possible for the device 2 to be constituted and dimensioned overall such that it can be comfortably worn on the body of the user. According to the invention, the device 2 is constituted such that the vessel parts 4, 8 disposed side by side can be positioned on the body in such a way that the second vessel part 8 is facing the body, that is, between the body and the first housing part 4 and the first housing part 4 is facing away from the body, that is, it essentially forms the visible side of the device 2. For that reason, the side 22 of the second housing part 8 facing the body of the user is rounded. As can be seen from FIGS. 1c, 1d, 3f, 3e, the side 22 facing the body is formed concavely seen in cross-section with a horizontal plane and comprises, for example, in the case shown, a radius of curvature R in some sections of, for example, 368 mm (FIGS. 1c, 3f). Additionally, the side 22 facing the body is also constituted concavely seen in cross-section with a vertical plane and has a radius of curvature R of, for example, 750 mm (FIG. 1d). In this way, the device 2 can be ergonomically disposed and worn in the hip region of a user.

It can also be seen that the second housing part 8 on its side 22 facing the body in an upper region and also on the side comprises a bevel 24 away from the body of the user toward the first housing part 4 or toward the side walls 26 and a circumferential facing end of the disk shape of the second housing part 8. The bevel 24, in the example shown here, runs about the full circumference; it extends from the standing side 28 from bottom to top, runs in an arc from there to the other side and then back down to the standing side 28.

It can also be seen from FIGS. 1d and 3 that, on the side 22 of the second housing part 8 facing the body, a grip recess 30 is formed in the shape of an opening extending right through the second housing part 8, and this in an upper region of the second housing part 8, slightly inclined away from the body. In this way, the device 2, or only its second housing part 8, can be gripped and handled with one hand.

Figure 2A:
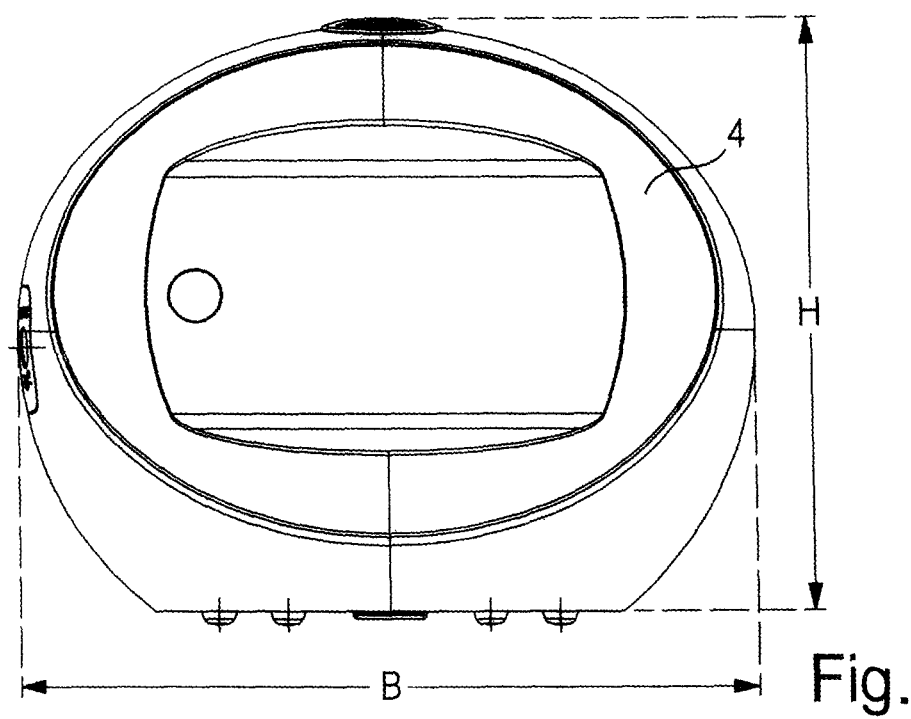
FIGS. 2a to e various views of a first housing part of the device according to FIG. 1, comprising a facility for generating a vacuum and control components.
Figure 2B:
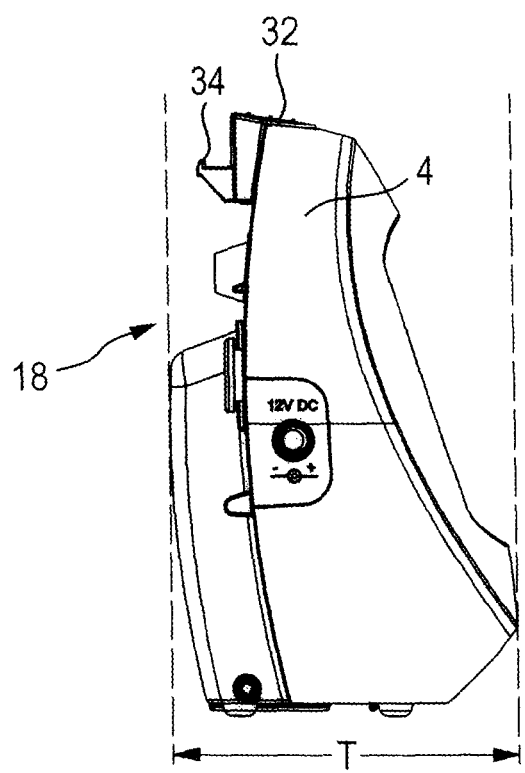
Figure 2C:
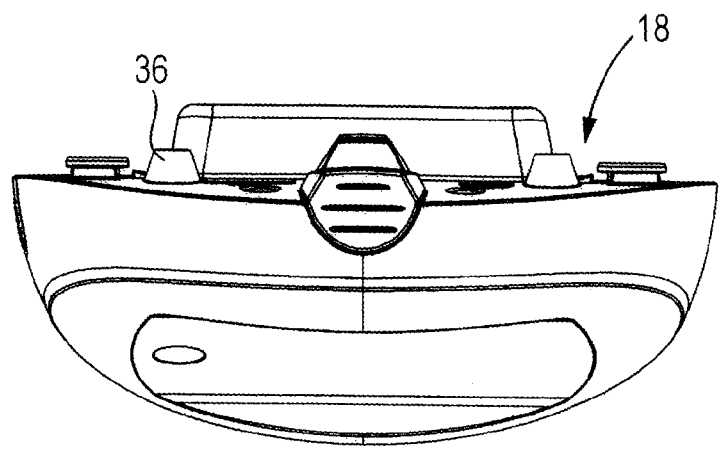
Figure 2D:
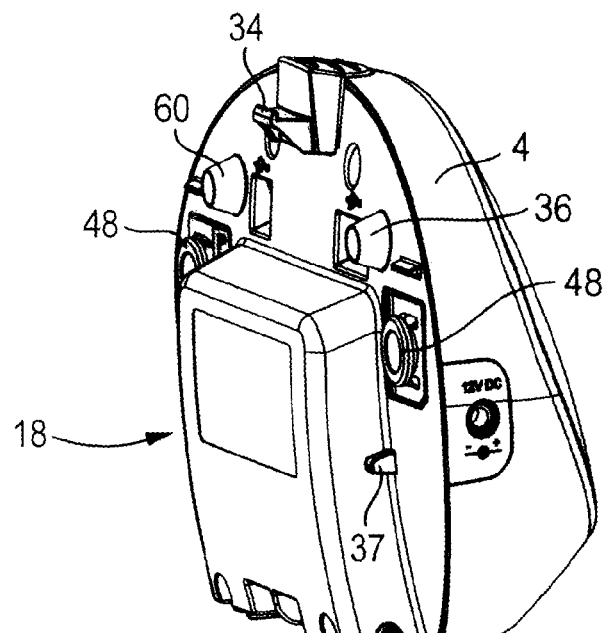
Figure 2E:
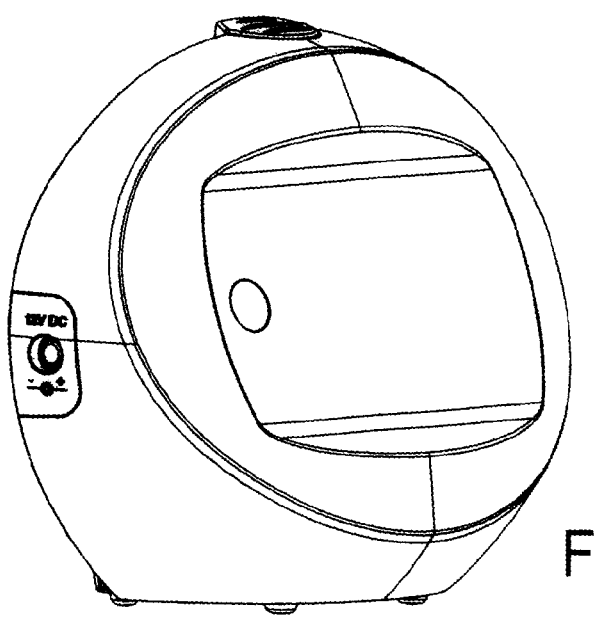
Figure 3F:
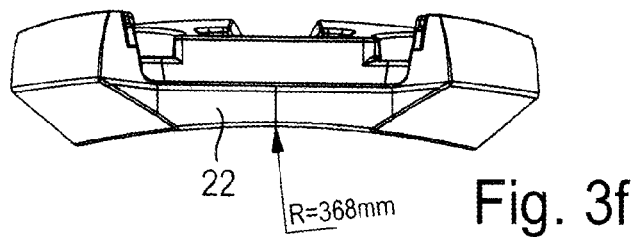
FIGS. 3a to i various views of a second housing part of the device according to FIG. 1, constituting a vessel to receive body fluids.
Figures 3A, 3B, 3C:
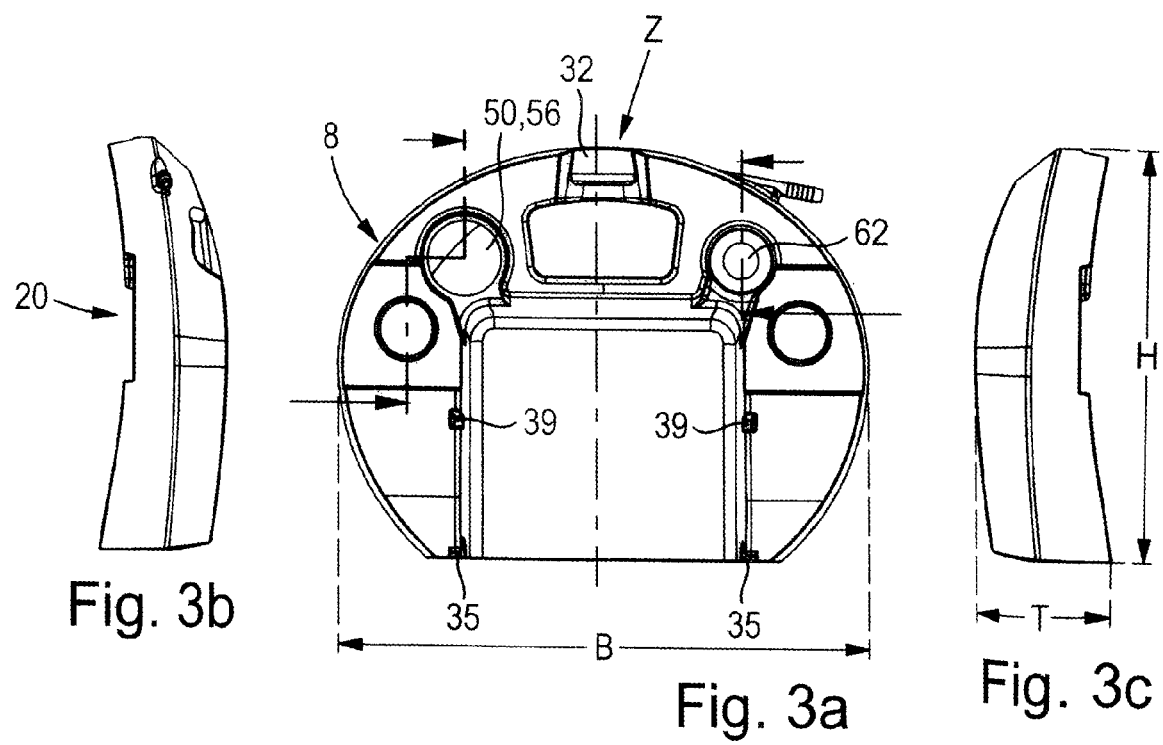
Figure 3E:
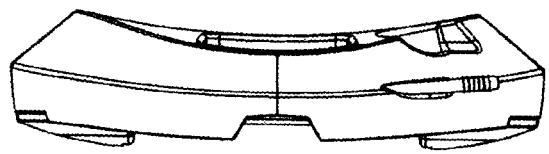
Figure 3D:
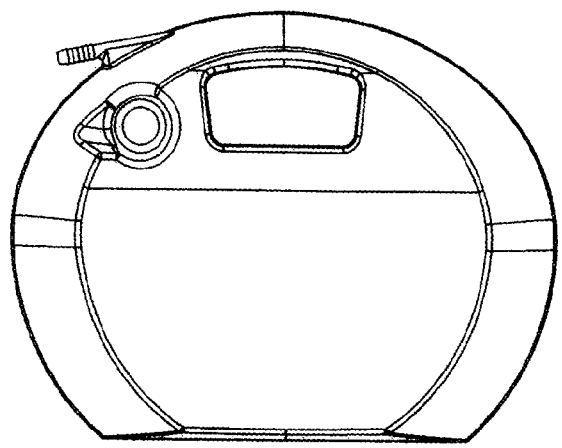
Figure 3G:
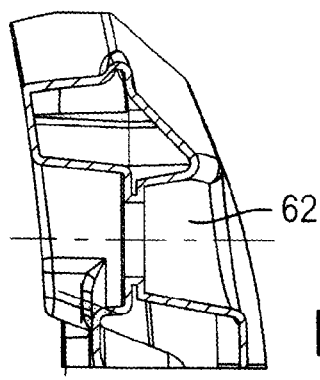
Figure 3H:
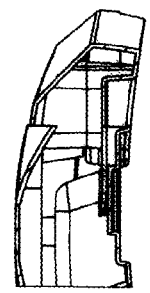
Figure 3I:
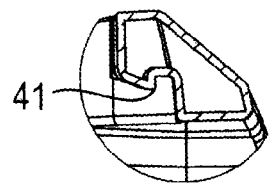
Figure 4A:
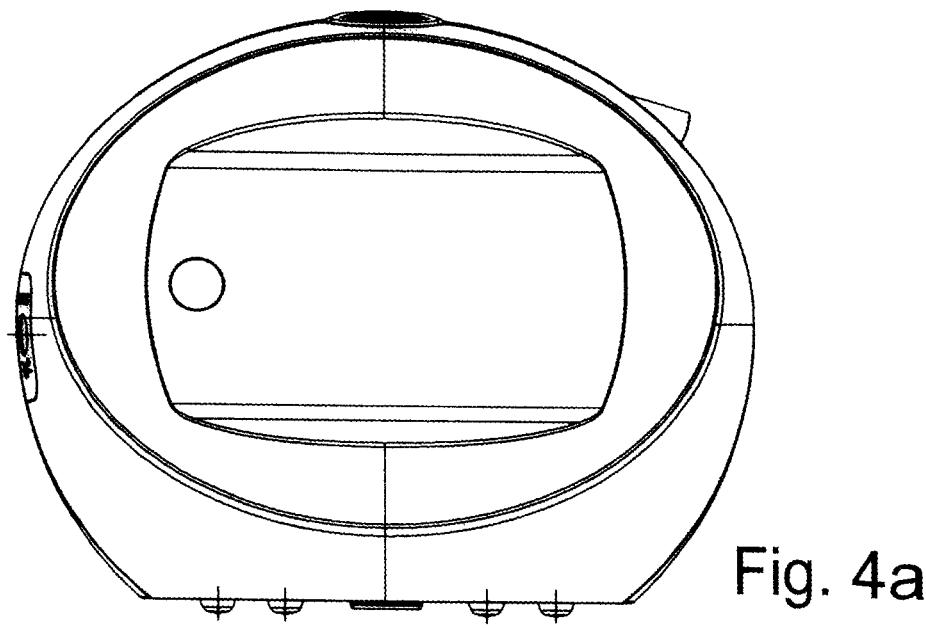
FIGS. 4a to e views corresponding to FIGS. 1a to e of a further embodiment of the device, wherein the second housing part is dimensioned larger than in the device according to FIGS. 1a to e.
Figure 4B:
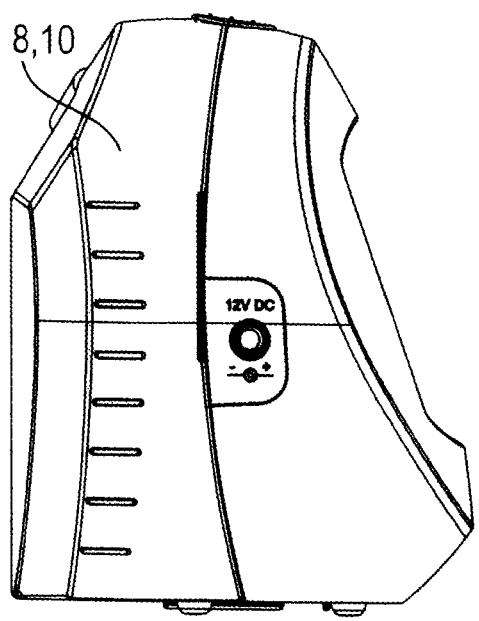
Figure 4C:
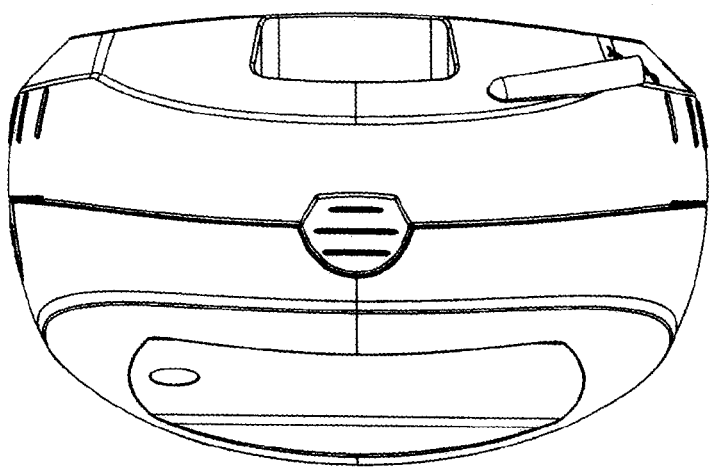
Figure 4D:
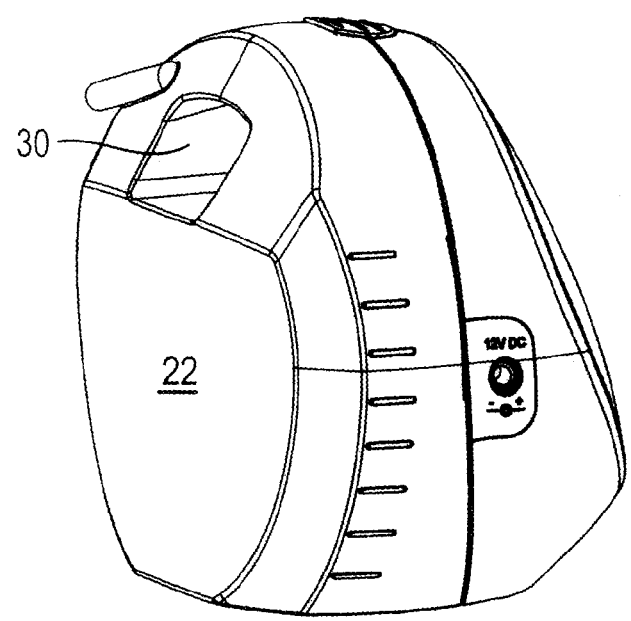
Figure 4E:
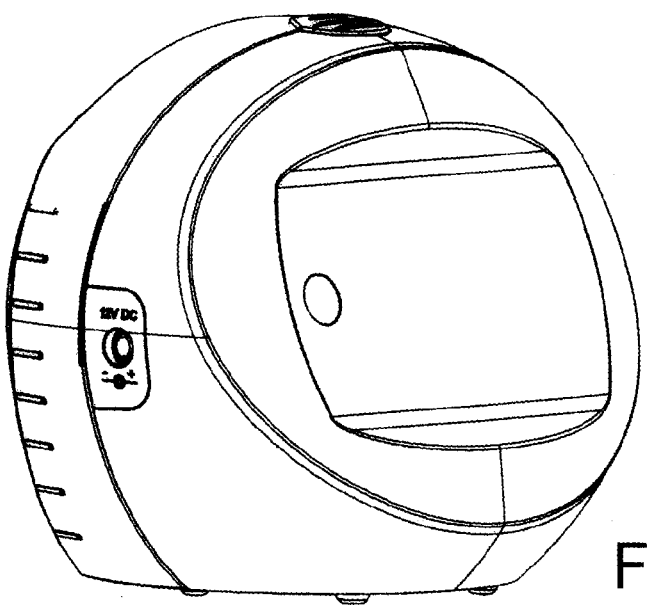

In the preferred embodiment shown, a manually operable element 32 is provided proximate to this grip recess 30 on the upper side of the device 2, for example, in the form of a pushbutton that acts on the locking and back-gripping means 34 (see FIGS. 2b and 2d). In the joined condition of the two housing parts 4 and 8, the locking or back-gripping means 34 are in a locked condition holding the two housing parts 4, 8 together by positive action. Only on operation of the operating element 32, is the lock released so that the housing parts 4, 8 can be separated. By the disposition and constitution of the grip recess 30 and the manually operable element 32 close together and such that a user can grip both in the grip recess 30 and also operate the operating element 32 with one finger of the same hand, a single-hand action for release of the second housing part 8 from the first housing part 4 is implemented. This proves especially advantageous because in that case a second housing part 8 filled with body fluids can be released with just one hand and placed in a disposal vessel.

To join the two housing parts 4, 8, the second housing part 8 is placed at a slight inclination from the rear and upward with its lower edge on two spigots forming a pivot 33 (FIG. 2d) of the first housing part 4. In the second housing part, a recessed region 35 (FIG. 3a) is formed on the lower edge to receive the spigot 33. If spigot 33 and the recessed region 35 are engaged, the second housing part 8 can be pivoted against the first housing part 4. In this way, the sides 18, 20 facing each other are placed one upon the other and thus enter the intended position with self-centering (supported by further guidance or centering means 37 (FIG. 2d) and 39 (FIG. 3a) and the complementary shapes of the sides 18, 20 of the housing parts 4,8 facing each other). By moving the two housing parts 4, 8 one against the other, in particular, essentially transversely with respect to the vertical separation plane 14, the locking and back-gripping means 34 is automatically deflected and then latches in the position that locks the housing parts 4, 8 one against the other. For this purpose, a latching hook 41 is provided on the second housing part 8 (FIG. 3i) under which the locking or back-gripping means 34 grips. If the housing parts 4, 8 are put in their locked position, vacuum communication is then automatically established between the interior of the vessel 10 of the second housing part 8 and the vacuum-generating facility through connection means 36 (described later in connection with FIG. 5).

A visible side 38 of the first housing part 4 facing away from the body is constituted with a slight inclination from the vertical so that the shape of the disk tapers in the upward direction. In this way, the visible side 38 can be more easily seen. Operating elements 40 and display elements 42, in particular, in the form of a touchscreen are provided there. Essentially, the entire visible side 38 is overlapped or constituted by a large-surface cover 44 so that no dirt-trapping joints are formed in the region of the operating elements 40.

Moreover, the figures show, in the region of the separation plane 14 between the contacting housing parts 4, 8, a plug slot 46 for plugging and releasably fixing a fastening means, in particular, and preferably in the form of a flexible belt, or a bow or a strap, on which, for example, a belt or a carrying shoulder strap can be fastened, or in another form. It proves advantageous if this fastening means can be separated from the housing parts 4, 8 and is therefore no obstacle if the device 2 is used in stationary operation, that is, standing on a preferably level surface 16, for example, if a patient to be treated with the device 2 is resting in a hospital bed. FIG. 2d indicates, on the side 18 of the first housing part 4, means 48 on which the fastening means plugged into the plug slot 46 are fixed or held.

The further embodiment of the inventive device shown in FIGS. 4a to e differs from the embodiment shown in FIG. 3 in that the second housing part 8 and the vessel 10 constituted by it has a larger volume. The bevel in the upper region of the side 22 of the second housing part 8 facing the body, in which the grip cavity 30 is formed, is somewhat more inclined away from the body of the user. This permits even better access. This larger second housing part 8 is more suitable for stationary operation of the device 2; it could have an outwardly convex side 22 for this purpose or even be formed with a greater protrusion than is shown in FIG. 4.

Figure 5:
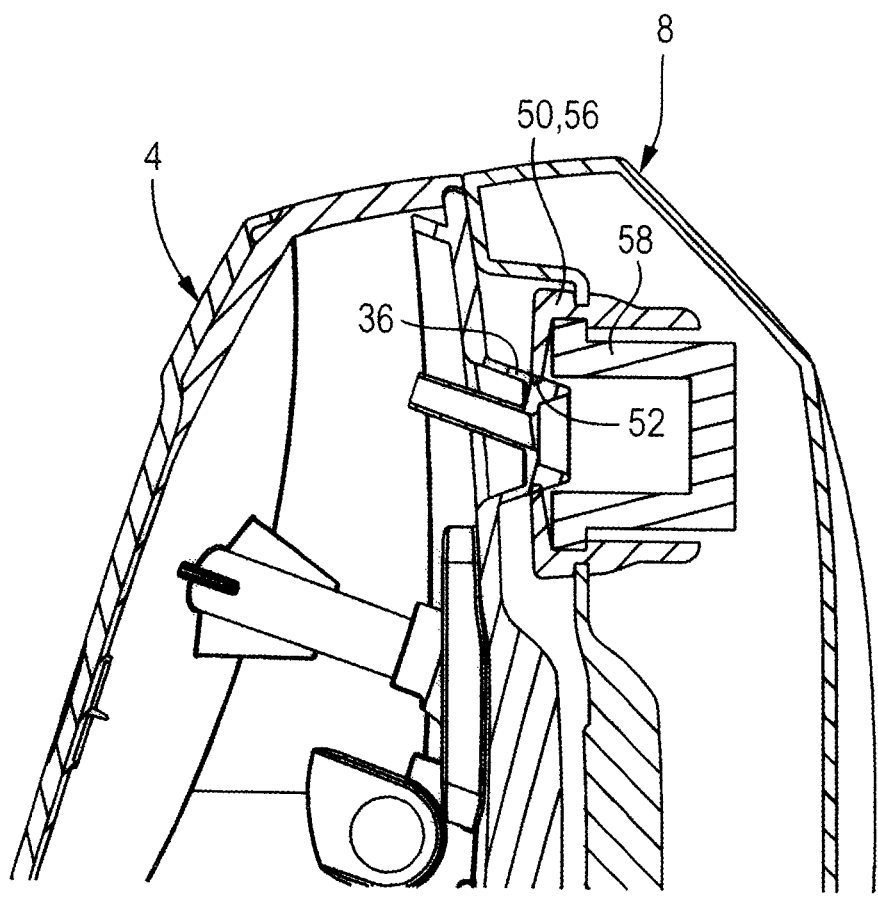
FIG. 5 a sectional view through the device in the region of the vacuum communication between the first and the second housing part.

FIG. 5 shows in detail the nature of the vacuum communication between the interior of the second housing part 8 constituting the vessel 10 and the first housing part 4. The suction side of a vacuum-generating facility, not depicted, leads to the conically shaped connection means 36 that tapers conically toward the second housing part 8. In this way, an at least slightly compliant mating connection means 50 of the second housing part 8 that, in the example shown, has a circular opening 52 that is bounded by a compliant sealing lip 54, can be applied with sealing, against the conical connection means 36 of the first housing part 4. This mating connection means 50 exits into the interior of the second housing part 8. It also forms a filter receiving means 56 for a filter 58 that, in the example shown, is constituted as a cup-shaped filter and prevents bacteria from being suctioned into the first housing part 4. It is immediately apparent that, on moving the two housing parts 4, 8 one against the other, the connection means 36 of the first housing part 4 forms a pressure communication sealed outwardly with the mating connection means 50 of the second housing part 8.

The coupling between the connection 13 for a measuring or rinsing duct and the associated also exemplary conically formed connection means 60 on the first housing part 4 is formed in a similar way. As can be seen from FIG. 3g, a coupling or grommet part, not depicted, can be inserted into the passage opening 62 in the second housing part 8 that then forms the connection 13 shown in FIG. 1d for the measuring or rinsing duct. This coupling or grommet part, not depicted, can then be coupled pressure-tight with the conical connection means 60. In this way, a liquid medium, in particular, air or a rinsing liquid can be guided into the wound through a tube to support the removal by suction of wound exudates. A measuring or rinsing tube and the suction tube are typically accessories for the second housing part that are single-use components; they are disposed of together with the second housing part after use.

Finally, FIGS. 6 and 7 illustrate differently sized standing surfaces 64 (with approx. 7 cm$^2$) and 66 (with approx. 55 cm$^2$) with differently sized second housing parts 8 of the embodiments according to FIGS. 1 and 4. The housing parts 8 can be set down on a surface on these standing surfaces 64 or 66 if they are removed from the first housing part 4. If they are held on the first housing part 4, the standing surface of the device 2 is constituted by the first housing part 4. Foot elements can also be provided on the standing surfaces of the housing parts 4, 8, as can be seen from the FIGS. 1b, 2b, and 4b.

FIG. 8 shows an inventive device for generating a vacuum for medical applications referred to collectively by reference symbol 2 and a holding facility 102 that interacts therewith but is shown in the detached state. This FIG. 8 only shows an essentially rigid holding part 104 of the holding facility 102 constituted, by way of example, as a metal bent punched part which has a receptacle 106 for a compliant and preferably elastically compliant ribbon-shaped holding means 108 which is shown in the following figures. The rigid holding part 104 is constituted as a detachable fastening on the first housing part 4 of the device 2. For this purpose, a threaded hole 112 is constituted on the underside 110 of the first housing part into which a clamping screw that can be tightened and released manually and screwed, preferably without the use of tools. The rigid holding part 104 has a through-hole 116 for this purpose in a preferably flat and wide contact area 118.

The holding part 104 is bent from a flat metal material section into the angular shape shown in FIGS. 9a and 9b. If the holding part 104 is fastened against the first housing part 4 of the device 2 by means of the clamping screw 114 perpendicularly to the drawing plane in FIG. 8 with the relevant plane of its sections, the second housing part 8, which constitutes the vessel 10 for receiving liquids is disposed between the one leg 120 of the rigid holding part 104 and the first housing part 4 of the holding facility 2. The other leg 122 of the rigid holding part 104 extends below the vessel 8.

It can be seen from FIG. 8 ff that the receptacle 106 constituted on the holding part 104 is constituted as a sliding-seat configuration. It comprises for this purpose a finger-shaped or tongue-shaped freely ending web 124 that is constituted by punching out from the flat metal material section, although other shapes are also conceivable.

From the detailed view in FIG. 9b, it can be seen that the relevant web 124 becomes flatter or beveled 126 at its free end, that is, it is tapered. This makes it easier to push it onto or over the ribbon-like holding means 108 that has yet to be described.

Figure 10C:
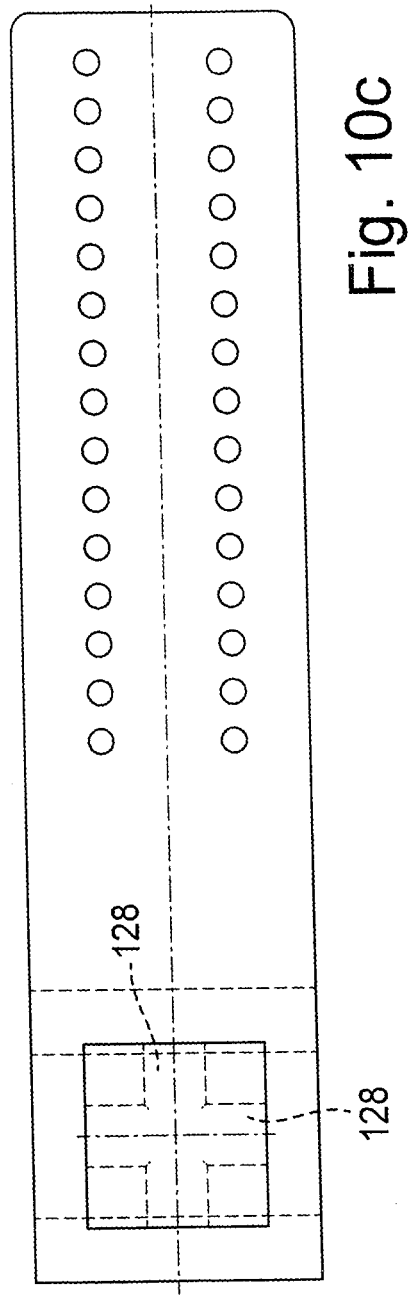

FIGS. 10a and b show a side view and perspective view of the flexible ribbon-shaped holding means 108, which is made of an, in particular, elastically compliant material, in particular, based on rubber, silicone, polymer. To connect to the rigid holding part 104, the ribbon-like holding means 108 comprises a duct-forming cutout 128 corresponding to the geometry of the tongue-shaped webs 124, with which the ribbon-like holding means 108 can be pushed onto either one of the webs 124 and can therefore be in any of the various configurations shown in FIGS. 11a, b. As can be seen even more clearly from FIG. 10c, two duct-forming cutouts 128 extend mutually perpendicularly so that the ribbon-like holding means 108 can be pushed onto the finger-shaped webs 124 of the rigid holding part 104 in various alignments (see FIGS. 11a, b).

In the case of a ribbon-like holding means 108 according to FIGS. 10a, b, a rigid, preferably metal reinforcing part 130 is provided in addition to the flexible ribbon-like material, which has through-holes 132 and is molded into the compliant material by casting or injection. The reinforcing part 130 extends out of the compliant material with two projections 134 by way of example. These projections 134 together with hole-pattern-like openings 136 form mechanical-action closure means 138 in the ribbon-like holding means 108. The section with the openings 136 of the ribbon-like holding means 108 can be placed around a vertical or horizontal strut of a patient bed or infusion stand and two of the openings 136 can be made to engage with the projections 134 by exerting tensile force so that clearance-free disposition can be achieved under tensile strain. The design with a reinforcing part 130 proves advantageous. However, it is at least basically conceivable that no such reinforcing part is present (as shown in FIG. 10c). In this case, appropriate projections on the rigid holding part 104 or in another manner on the ribbon-like holding means 108 could be provided.

The flexible ribbon-shaped holding means 108 also has a thicker section 140, within which the stated reinforcing part 130 is held. This thicker region 140 is constituted three-dimensionally contoured transversely with respect to the ribbon plane. It has an approximately concave contact zone 142 with which the holding facility can be contacted with an elongated strut or bar. Because the contact zone 142 is also constituted to be compliant, preferably elastically compliant, large wide-surface contact with the strut or bar can be achieved.

Figure 11A:
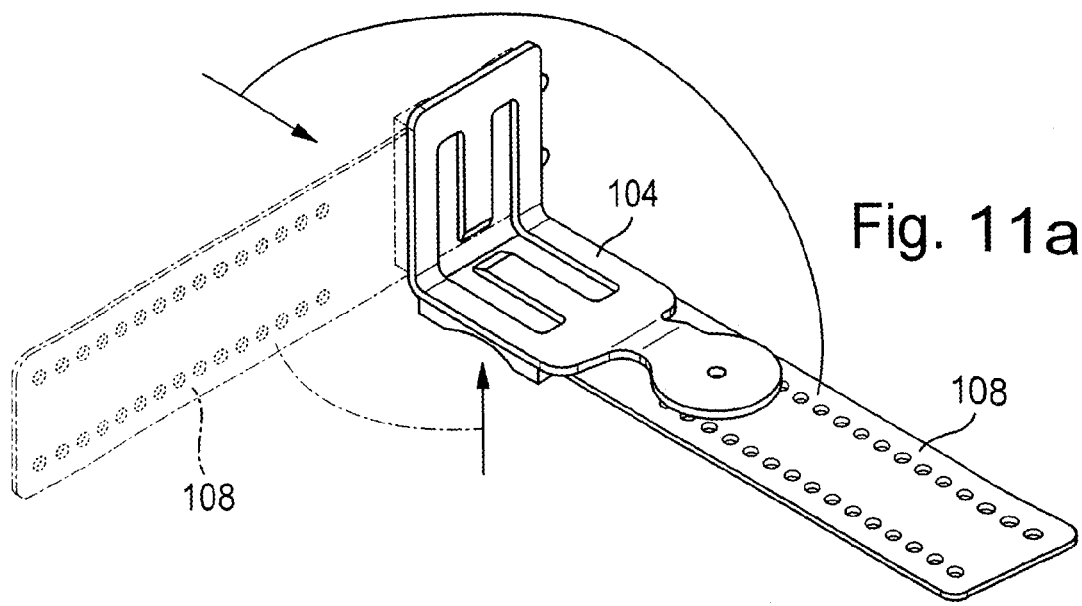
FIGS. 11a, b illustrate the orientation of the ribbon-like holding means on the rigid holding part.
Figure 11B:
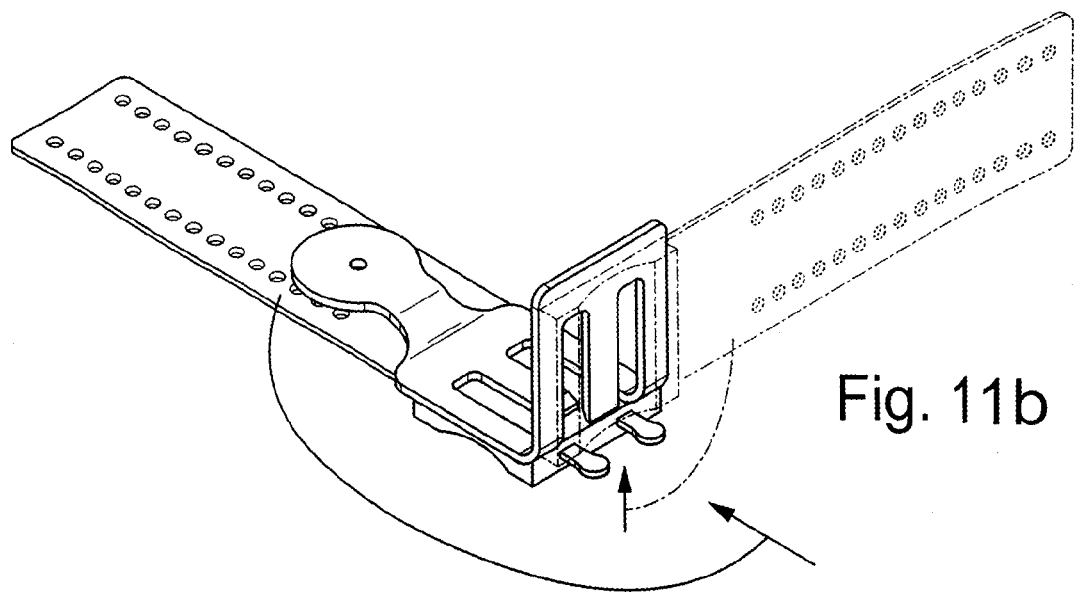

In FIGS. 11a and b, arrows indicate the push-on direction for each ribbon-like holding means 108 associated with the relevant arrow. Each ribbon-like holding means 108 with its two mutually perpendicular duct-forming cutouts 128 can be disposed in four orientations on the relevant finger-shaped web 124 of the rigid holding part 104 so that a total of eight different configurations of two ribbon-like holding means 108 with respect to the rigid holding part can be provided.

Overall, the inventive embodiment of the device 2 and the holding facility 102 permits fast and user-friendly mounting of the device on a patient bed, an infusion stand, or the like.

We claim:

1. A device for generating vacuum for medical applications or for vacuum therapy of wounds on a human or animal body, the device comprising:
   a housing;
   a vacuum generator disposed in said housing;

a vessel for receiving body fluids or wound exudates suctioned out of a wound, said vessel structured for detachable fastening to said housing;

a connection element, said connection element structured for connection to a suction tube adapted to lead to the body, thereby establishing vacuum communication among said vacuum generator, said vessel and the suction tube; and a holding facility for detachable fastening of the device onto a horizontal, vertical or oblique strut or bar, said holding facility comprising an essentially rigid holding part and at least one flexible or elastically compliant ribbon-shaped holding strap, said holding part structured for attachment to and detachment from said housing, said holding part having at least one receptacle for detachable disposition of said holding strap, said holding strap structured for placement around the strut or bar, said holding strap also being structured to turn back on itself or onto said holding part, wherein said holding strap is closed in response to exercise of a tensile force thereon, thereby generating a substantially clearance-free and clamped fastening of the device to the strut or bar, wherein said essentially rigid holding part can be detachably fastened to said housing by means of a screw fastening, wherein, towards that end, a threaded hole is defined in said housing for acceptance of a threaded bolt.

2. A device for generating vacuum for medical applications or for vacuum therapy of wounds on a human or animal body, the device comprising:

a housing;

a vacuum generator disposed in said housing;

a vessel for receiving body fluids or wound exudates suctioned out of a wound, said vessel structured for detachable fastening to said housing;

a connection element, said connection element structured for connection to a suction tube adapted to lead to the body, thereby establishing vacuum communication among said vacuum generator, said vessel and the suction tube; and a holding facility for detachable fastening of the device onto a horizontal, vertical or oblique strut or bar, said holding facility comprising an essentially rigid holding part and at least one flexible or elastically compliant ribbon-shaped holding strap, said holding part structured for attachment to and detachment from said housing, said holding part having at least one receptacle for detachable disposition of said holding strap, said holding strap structured for placement around the strut or bar, said holding strap also being structured to turn back on itself or onto said holding part, wherein said holding strap is closed in response to exercise of a tensile force thereon, thereby generating a substantially clearance-free and clamped fastening of the device to the strut or bar, said receptacle for detachable disposition of said holding strap constituting a sliding-seat configuration, wherein said holding strap is pushed onto said rigid holding part in a linear direction, said receptacle having at least one finger-shaped or tongue-shaped web or a flat web, which engages in a duct-forming cutout of said holding strap when said holding strap is pushed on.

3. The device of claim 2, wherein said receptacle is constituted in such a way that said holding strap can be fastened in two orientations of a longitudinal axis thereof that extend at 90° to each other.

4. The device of claim 2, wherein said holding part has at least two receptacles, each for detachable disposition of one holding strap, said receptacles being oriented such that said holding straps are aligned at an angle of 90° with respect to each other and with respect to the device.

5. The device of claim 2, wherein said holding part has an angular shape defining two legs.

6. The device of claim 5, wherein one receptacle for detachable disposition of one holding strap is constituted on each leg of said holding part.

7. The device of claim 2, wherein said holding strap has two mutually perpendicular duct-forming cutouts.

8. The device of claim 2, wherein said holding strap has a mechanical-action closing element, said closing element being turned back on itself or onto said holding part for closure thereof, said mechanical-action closing element being constituted by at least one projection on one side and by through-holes on an other side.

9. The device of claim 8, wherein said at least one projection extends in a plane of said holding strap or in a plane of said holding part.

10. The device of claim 8, wherein said holding strap has a reinforcing part constituted as a rigid or injection molded part, said reinforcing part defining said at least one projection.

11. The device of claim 2, wherein said holding strap has a thicker region that is constituted with 3-dimensional contouring in a transverse direction with respect to a ribbon plane, to form a compliant contact zone for contacting the bar or strut.

12. The device of claim 2, wherein said holding part is constituted in such a way that said vessel for receiving liquids is disposed between said receptacle of said holding part and said housing.

13. The device of claim 2, wherein said holding facility and said holding part are constituted in such a way that variously dimensioned vessels are removable from said housing or mountable to said housing without any need to detach said holding facility.

14. A device for generating vacuum for medical applications or for vacuum therapy of wounds on a human or animal body, the device comprising:

a housing;

a vacuum generator disposed in said housing;

a vessel for receiving body fluids or wound exudates suctioned out of a wound, said vessel structured for detachable fastening to said housing;

a connection element, said connection element structured for connection to a suction tube adapted to lead to the body, thereby establishing vacuum communication among said vacuum generator, said vessel and the suction tube; and a holding facility for detachable fastening of the device onto a horizontal, vertical or oblique strut or bar, said holding facility comprising an essentially rigid holding part and at least one flexible or elastically compliant ribbon-shaped holding strap, said holding part structured for attachment to and detachment from said housing, said holding part having at least one receptacle for detachable disposition of said holding strap, said holding strap structured for placement around the strut or bar, said holding strap also being structured to turn back on itself or onto said holding part, wherein said holding strap is closed in response to exercise of a tensile force thereon, thereby generating a substantially clearance-free and clamped fastening of the device to the strut or bar, wherein said receptacle is constituted in such a way that said holding strap can be fastened in two orientations of a longitudinal axis thereof that extend at 90° to each other.

15. The device of claim 14, wherein said holding part has at least two receptacles, each for detachable disposition of one holding strap, said receptacles being oriented such that said holding straps are aligned at an angle of 90° with respect to each other and with respect to the device.

16. The device of claim 14, wherein said holding part has an angular shape defining two legs.

17. The device of claim 16, wherein one receptacle for detachable disposition of one holding strap is constituted on each leg of said holding part.

18. The device of claim 14, wherein said holding strap has two mutually perpendicular duct-forming cutouts.

19. The device of claim 14, wherein said holding strap has a mechanical-action closing element, said closing element being turned back on itself or onto said holding part for closure thereof, said mechanical-action closing element being constituted by at least one projection on one side and by through-holes on an other side, wherein said at least one projection extends in a plane of said holding strap or in a plane of said holding part.

20. The device of claim 14, wherein said holding strap has a mechanical-action closing element, said closing element being turned back on itself or onto said holding part for closure thereof, said mechanical-action closing element being constituted by at least one projection on one side and by through-holes on an other side, wherein said holding strap has a reinforcing part constituted as a rigid or injection molded part, said reinforcing part defining said at least one projection.

* * * * *